(12) United States Patent
Tseng et al.

(10) Patent No.: US 10,893,836 B2
(45) Date of Patent: Jan. 19, 2021

(54) PHYSIOLOGICAL SIGNAL PROGRESSING DEVICE

(71) Applicant: Industrial Technology Research Institute, Hsinchu (TW)

(72) Inventors: Kuo-Hua Tseng, New Taipei (TW); Chih-Wei Chen, Hsinchu County (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 72 days.

(21) Appl. No.: 16/232,661

(22) Filed: Dec. 26, 2018

(65) Prior Publication Data

US 2020/0178901 A1   Jun. 11, 2020

(30) Foreign Application Priority Data

Dec. 11, 2018 (TW) .............................. 107144454 A

(51) Int. Cl.
*A61B 5/0402* (2006.01)
*A61B 5/00* (2006.01)
(Continued)

(52) U.S. Cl.
CPC .......... *A61B 5/7207* (2013.01); *A61B 5/0205* (2013.01); *A61B 5/0402* (2013.01);
(Continued)

(58) Field of Classification Search
CPC .............. A61B 5/0205; A61B 5/02405; A61B 2/04012; A61B 5/0402; A61B 5/04085;
(Continued)

(56) References Cited

U.S. PATENT DOCUMENTS 6,496,715 B1 * 12/2002 Lee .................. A61N 1/375
600/424
8,613,708 B2   12/2013 Bishay et al.
(Continued)

FOREIGN PATENT DOCUMENTS

CN   101816557 A   9/2010
CN   105550734 A   5/2016
(Continued)

OTHER PUBLICATIONS

Taiwan Patent Office, Office Action, Patent Application Serial No. 107144454, dated Jul. 5, 2019, Taiwan.

*Primary Examiner* — George Manuel

(57) ABSTRACT

A physiological signal processing device is provided. The physiological signal processing device includes a patch, a plurality of electrodes and a processing device. The plurality of electrodes detect an Electrocardiography (ECG) signal. The processing device is configured in the patch and is coupled to the plurality of electrodes to receive the ECG signal. Furthermore, according to the ECG signal, the processing device calculates a first differential value between a voltage of an R wave of the ECG signal and a reference ECG value, and determines whether the first differential value is greater than or equal to a first threshold to determine whether to adjust the positions of the electrodes. When the positions of the electrodes are determined, the processing device obtains heartbeat information and/or breathing information according to the ECG signal.

23 Claims, 6 Drawing Sheets

(51) Int. Cl.
*A61B 5/0205* (2006.01)
*A61B 5/0408* (2006.01)
*A61B 5/04* (2006.01)
*A61B 5/0472* (2006.01)
*A61B 5/0456* (2006.01)
*A61B 5/08* (2006.01)
*A61B 5/024* (2006.01)

(52) U.S. Cl.
CPC ........ *A61B 5/04012* (2013.01); *A61B 5/0456* (2013.01); *A61B 5/0472* (2013.01); *A61B 5/04085* (2013.01); *A61B 5/684* (2013.01); *A61B 5/6833* (2013.01); *A61B 5/7264* (2013.01); *A61B 5/02405* (2013.01); *A61B 5/0816* (2013.01)

(58) Field of Classification Search
CPC ... A61B 5/0456; A61B 5/0472; A61B 5/0816; A61B 5/6833; A61B 5/684; A61B 5/7207; A61B 5/7264; A61B 5/7221
See application file for complete search history.

(56) References Cited

U.S. PATENT DOCUMENTS

| | | |
|---|---|---|
| 8,818,478 B2 | 8/2014 | Scheffler et al. |
| 9,433,380 B1 | 9/2016 | Bishay et al. |
| 9,619,660 B1 | 4/2017 | Felix et al. |
| 9,775,536 B2 | 10/2017 | Felix et al. |
| 9,955,885 B2 | 5/2018 | Felix et al. |
| 2007/0179388 A1* | 8/2007 | Larik ................. A61N 1/3702 600/508 |

FOREIGN PATENT DOCUMENTS

| | | |
|---|---|---|
| CN | 107049301 A | 8/2017 |
| CN | 107582045 A | 1/2018 |
| TW | 201031384 A | 9/2010 |
| TW | 201546429 A | 12/2015 |
| TW | 201617026 A | 5/2016 |

* cited by examiner

100

200

PHYSIOLOGICAL SIGNAL PROGRESSING DEVICE

CROSS REFERENCE TO RELATED APPLICATIONS

This Application claims priority of Taiwan Patent Application No. 107144454 filed on Dec. 11, 2018, the entirety of which is incorporated by reference herein.

BACKGROUND

Field of the Disclosure

The disclosure generally relates to a physiological signal processing device.

Description of the Related Art

In conventional electrocardiography (ECG) signal measurement technology, a multi-lead measurement method or a single-lead measurement method is used to measure the ECG signal. In the multi-lead measurement method, a plurality of electrode patches may be patched to different positions on the user's body to obtain the ECG signal of the user. Furthermore, in the multi-lead measurement method, the electrode patches could be moved to change the positions and distance between the electrode patches. In the single-lead measurement method, a patch may be patched to the user's body to obtain the ECG signal of the user through the two electrodes in the patch.

The ECG signal of the user could be obtained the more easily using the single-lead measurement method than using the multi-lead measurement method. However, because the distance of the two electrodes of the patch is fixed in the single-lead measurement method, the distance of the two electrodes of the patch could not be adjusted for the bodies of different users. Therefore, in ECG signal measurement, the single-lead measurement method could not meet the different requirements of different users.

SUMMARY

An embodiment of the disclosure provides a physiological signal processing device. The physiological signal processing device comprises a patch, a plurality of electrodes and a processing device. The plurality of electrodes detect an electrocardiography (ECG) signal. The processing device is configured in the patch and is coupled to the plurality of electrodes to receive the ECG signal. Furthermore, according to the ECG signal, the processing device calculates a first differential value between a voltage of an R wave of the ECG signal and a reference ECG value, and determines whether the first differential value is greater than or equal to a first threshold to determine whether to adjust the positions of the electrodes. When the positions of the electrodes are determined, the processing device obtains heartbeat information and/or breathing information according to the ECG signal.

Other aspects and features of the disclosure will become apparent to those with ordinary skill in the art upon review of the following descriptions of specific embodiments of the physiological signal processing device.

BRIEF DESCRIPTION OF THE DRAWINGS

The disclosure will become more fully understood by referring to the following detailed description with reference to the accompanying drawings, wherein.

DETAILED DESCRIPTION OF THE DISCLOSURE

The following description is made for the purpose of illustrating the general principles of the disclosure and should not be taken in a limiting sense. The scope of the disclosure is best determined by reference to the appended claims.

Figure 1:
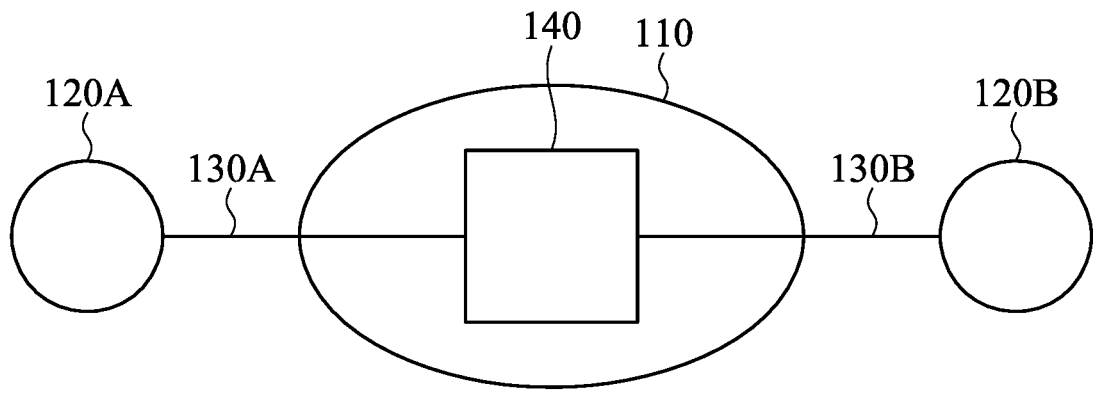
FIG. 1 is a schematic diagram of a physiological signal processing device 100 according to an embodiment of the disclosure.

FIG. 1 is a schematic diagram of a physiological signal processing device 100 according to an embodiment of the disclosure. As shown in FIG. 1, the physiological signal processing device 100 may comprise a patch 110, a first electrode 120A, a second electrode 120B, a first stretchable line 130A, a second stretchable line 130B, and a processing device 140. In order to clarify the concept of the disclosure, FIG. 1 presents a simplified block diagram in which the elements relevant to the disclosure are shown. However, the disclosure should not be limited to what is shown in FIG. 1.

According to an embodiment of the disclosure, the processing device 140 may be a microprocessor or a microcontroller, but the disclosure should not be limited thereto.

As shown in FIG. 1, in the disclosure, the processing device 140 may be configured in the patch 110. The first electrode 120A and the second electrode 120B may be respectively coupled to the processing device 140 through the first stretchable line 130A and the second stretchable line 130B. The positions of the first electrode 120A and the second electrode 120B patched may be adjusted through the first stretchable line 130A and the second stretchable line 130B.

When the ECG signal measurement is performed for the user, the patch 110 of the physiological signal processing device 100 may be patched on the body of the user. Then, the ECG signal measurement function of the physiological signal processing device 100 is enabled, and the initial parameter configuration for the ECG signal measurement is performed. Then, the first electrode 120A and the second electrode 120B are patched on the user's body to obtain the ECG signal of the user. When the first electrode 120A and the second electrode 120B are patched, the first electrode 120A and the second electrode 120B may extract the ECG signal of the user and transmit the extracted ECG signal to the processing device 140. According to an embodiment of the disclosure, the first electrode 120A and the second electrode 120B may extract at least of two periods (e.g. 3 second) of ECG signal.

When the processing device 140 obtains the ECG signal, the processing device 140 may capture the R wave of the ECG signal from the ECG signal, and then the processing device 140 may calculate a first differential value between the voltage Rp of the R wave and a reference ECG value Bn, and obtain the absolute value of the first differential value (i.e. abs|Rp−Bn|, which is directly referred to as the first differential value below in the disclosure). Then, the processing device 140 may determine whether the first differential value is greater than or equal to (i.e. ≥) a first threshold Va to determine whether to adjust the positions of the first electrode 120A and the second electrode 120B.

When the first differential value is not greater than or equal to a first threshold Va, it means that the signal strength of the R wave of the ECG signal is not sufficient. Therefore, the positions of the first electrode 120A and the second electrode 120B will be adjusted to extract a new ECG signal. It should be noted that in the embodiment, the adjustment of the first electrode 120A and the second electrode 120B is a coarse adjustment, e.g. the movement distance of the first electrode 120A and the second electrode 120B is over 1 cm, but the disclosure is not limited thereto. When the positions of the first electrode 120A and the second electrode 120B have been adjusted, the first electrode 120A and the second electrode 120B may start to extract a new ECG signal and transmit the new extracted ECG signal to the processing device 140. The processing device 140 may analyze the new extracted ECG signal.

When the first differential value is greater than or equal to a first threshold Va, it means that the signal strength of the R wave of the ECG signal is sufficient. Therefore, the processing device 140 may capture the Q wave of the ECG signal from the ECG signal, and then the processing device 140 may calculate a second differential value between the voltage Qp of the Q wave and the reference ECG value Bn, and obtain the absolute value of the second differential value (i.e. abs|Qp−Bn|, which is called the second differential value hereinafter). In addition, the processing device 140 may capture the S wave of the ECG signal from the ECG signal, and then the processing device 140 may calculate a third differential value between the voltage Sp of the Q wave and the reference ECG value Bn, and obtain the absolute value of the third differential value (i.e. abs|Sp−Bn|, which is called the third differential value hereinafter). Then, the processing device 140 may determine whether the second differential value is greater than or equal to (i.e. ≥) a second threshold Vb and determine whether the third differential value is greater than or equal to (i.e. ≥) a third threshold Vc. In addition, the processing device 140 may further determine whether the signal-to-noise ratio (SNR) of the ECG signal is greater than or equal to (i.e. ≥) the SNR of the R wave, and/or the SNR of the Q wave, and/or the SNR of the S wave.

When the second differential value is not greater than or equal to the second threshold Vb, the third differential value is not greater than or equal to the third threshold Vc, or the SNR of the ECG signal is not greater than or equal to the SNR of the R wave, and/or the SNR of the Q wave, and/or the SNR of the S wave, it means that the signal strength of the Q wave or the signal strength of the S wave of the ECG signal is not sufficient. Therefore, the positions of the first electrode 120A and the second electrode 120B will be adjusted to extract a new ECG signal. It should be noted that in the embodiment, because the R wave of the ECG signal has passed the decision, the adjustment of the first electrode 120A and the second electrode 120B is a fine adjustment, e.g. the movement distance of the first electrode 120A and the second electrode 120B is less than 1 cm, but the disclosure is not limited thereto. When the positions of the first electrode 120A and the second electrode 120B have been adjusted, the first electrode 120A and the second electrode 120B may start to extract a new ECG signal and transmit the new extracted ECG signal to the processing device 140. The processing device 140 may analyze the new extracted ECG signal.

When the second differential value is greater than or equal to the second threshold Vb, the third differential value is greater than or equal to the third threshold Vc, and the SNR of the ECG signal is greater than or equal to the SNR of the R wave, and/or the SNR of the Q wave, and/or the SNR of the S wave, it means that the ECG signal could content the requirements of the R wave, the Q wave and the S wave, and the signal strengths of the R wave, the Q wave and the S wave are all sufficient. Therefore, the processing device 140 may start to calculate the heartbeat information and/or the breathing information according to the ECG signal.

According to an embodiment of the disclosure, the processing device 140 may use a plurality of heartbeat algorithms to calculate the heartbeat information (i.e. the result of the heartbeat algorithms) according to the obtained ECG signal. For example, the processing device 140 may calculate the interval between each R wave (R–R interval, RRI). Then, the processing device 140 may calculate the heart rate (HR) and the heart rate variability (HRV) of the user according to the obtained RRI values. According to an embodiment of the disclosure, before the processing device 140 use the heartbeat algorithms to generate the heartbeat information of the user, the processing device 140 may determine whether to execute a smoothing algorithm according to the requirement of the physiological signal processing device 100. When the ECG signal is processed through the smoothing algorithm, the noise interference may be reduced to make the ECG signal become smooth and stable to increase the accuracy of generating the heartbeat information later.

According to an embodiment of the disclosure, the processing device 140 may determine whether the RRI value is in a default range. For example, the processing device 140 may determine whether the RRI value is greater than or equal to a first time threshold TL and smaller than or equal to a second time threshold TH (i.e. TL≤RRI≤TH). If the RRI value is not greater than or equal to the first time threshold TL or not smaller than or equal to a second time threshold TH, the processing device 140 may determine the ECG signal corresponding to the RRI value is not normal. Therefore, the processing device 140 may filter the ECG signal corresponding to the RRI value.

In another embodiment of the disclosure, the processing device 140 may determine whether the RRI value is larger than or equal to a default threshold. For example, the processing device 140 may determine whether the RRI value is greater than or equal to a time threshold TL (i.e. TL≤RRI). If the RRI value is not greater than or equal to the time threshold TL, the processing device 140 may determine the ECG signal corresponding to the RRI value is not normal. Therefore, the processing device 140 may filter the ECG signal corresponding to the RRI value.

In another embodiment of the disclosure, the processing device 140 may determine whether the RRI value is smaller than or equal to a default threshold. For example, the processing device 140 may determine whether the RRI value is smaller than or equal to a time threshold TH (i.e. RRI≤TH). If the RRI value is not smaller than or equal to a time threshold TH, the processing device 140 may determine the ECG signal corresponding to the RRI value is not normal. Therefore, the processing device 140 may filter the ECG signal corresponding to the RRI value.

According to an embodiment of the disclosure, the processing device 140 may use a breathing algorithm to calculate the breathing information (i.e. the result of the breathing algorithms) according to the obtained ECG signal. For example, the processing device 140 may obtain the breathing information through the ECG-derived respiration (EDR) algorithm or the frequency mixing signal division algorithm for the heartbeat and breathing signals. According to an embodiment of the disclosure, after the processing device 140 uses the breathing algorithm to generate the breathing information of the user, the processing device 140 may determine whether to enable a smoothing function for the breathing signal according to the requirement of the physiological signal processing device 100. When the breathing signal is processed through the smoothing function, the noise interference may be reduced to make the breathing signal become smooth and stable to increase the accuracy of generating the breathing information later.

According to an embodiment of the disclosure, when the processing device 140 obtains the heartbeat information and the breathing information of the user, the processing device 140 may store the heartbeat information and the breathing information of the user, and the position information of the electrodes of the physiological signal processing device 100 in a storage device (not show in figures) of the physiological signal processing device 100.

According to an embodiment of the disclosure, the processing device 140 may perform the machine learning according to the position information of the electrodes through a machine learning algorithm. When the samples of the machine learn are sufficient, when the user needs to measure the ECG signal, the electrodes (e.g. first electrode 120A and second electrode 120B) of the physiological signal processing device 100 may be directly patched on the position which is found according the machine learning.

According to an embodiment of the disclosure, the physiological signal processing device 100 may comprise a communication device (not shown in figures). The communication device may transmit the heartbeat information and the breathing information of the user to an electronic device (e.g. a smart phone, tablet, notebook, etc.) through a wireless communication technology (e.g. Bluetooth or Wi-Fi, but the disclosure is not limited thereto). According to an embodiment of the disclosure, the above operations (i.e. the analysis for the ECG signals) performed in the physiological signal processing device 100 may be performed by the electronic device. In other words, when the physiological signal processing device 100 obtains the ECG signal of the user, the physiological signal processing device 100 may transmit the obtained ECG signal to the electronic device, and then the electronic device may perform following operations as recited in the above embodiments.

Figure 2:
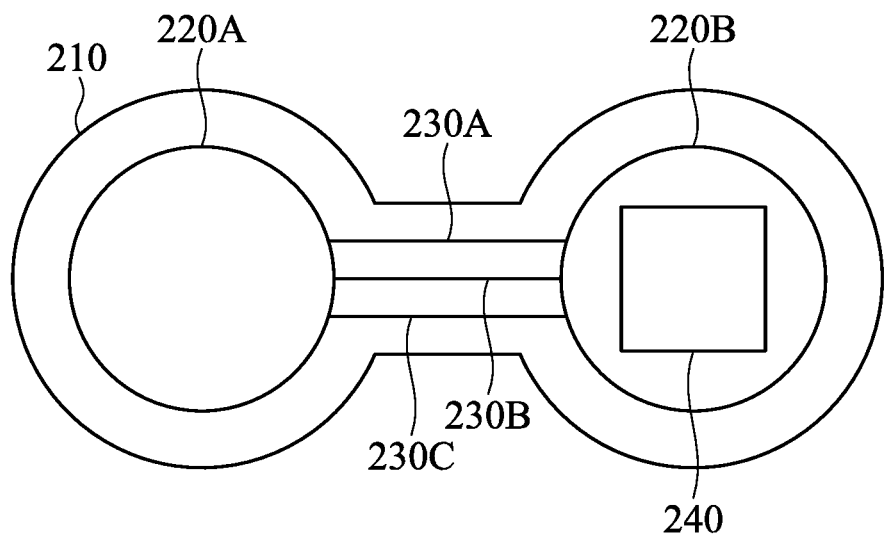
FIG. 2 is a schematic diagram of a physiological signal processing device 200 according to another embodiment of the disclosure.

FIG. 2 is a schematic diagram of a physiological signal processing device 200 according to another embodiment of the disclosure. As shown in FIG. 2, the physiological signal processing device 200 may comprise a patch 210, a first electrode 220A, a second electrode 220B, stretchable lines 230A-230C, and a processing device 240. In order to clarify the concept of the disclosure, FIG. 2 presents a simplified block diagram in which the elements relevant to the disclosure are shown. However, the disclosure should not be limited to what is shown in FIG. 2. It should be noted that the number of stretchable lines may be one, two, or other number, i.e. the disclosure is not limited to what is shown in FIG. 2.

According to an embodiment of the disclosure, the processing device 240 may be a microprocessor or a microcontroller, but the disclosure should not be limited thereto.

As shown in FIG. 2, unlike the physiological signal processing device 100, in the embodiment, the first electrode 220A, the second electrode 220B, the stretchable lines 230A-230C and the processing device 240 are configured in the patch 210. The first electrode 220A may be connected to the second electrode 220B through the stretchable lines 230A-230C, and the first electrode 220A and the second electrode 220B are coupled to the processing device 240. The position of the first electrode 220A and the second electrode 220B patched may be adjusted through the stretchable lines 230A-230C. In other words, in the embodiment, the patch 210 may be made of a stretchable material and the patch 210 could be stretched as the stretchable lines 230A-230C are stretched. In addition, because the operations of the processing device 240 are similar to the operations of the processing device 140, the details will not be discussed again.

Figure 3:
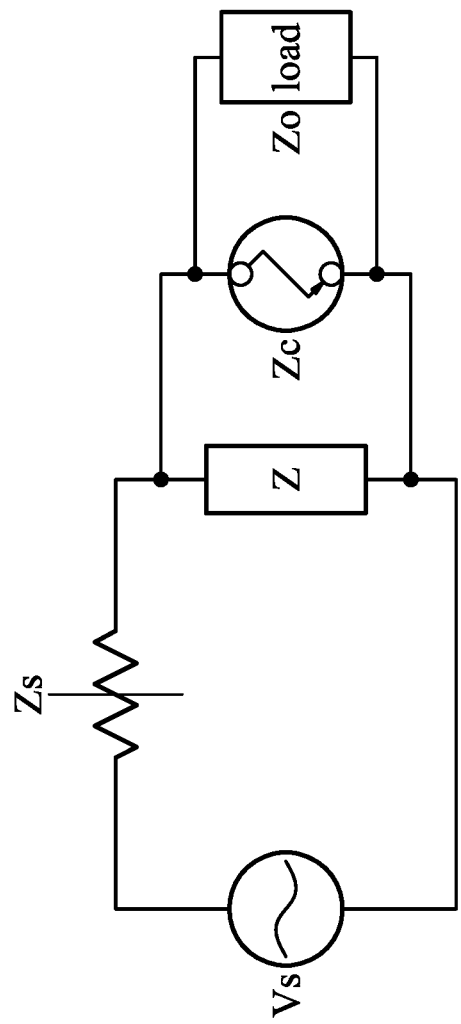
FIG. 3 is an equivalent schematic diagram of a compensation device 300 according to an embodiment of the disclosure.

FIG. 3 is an equivalent schematic diagram of a compensation device 300 according to an embodiment of the disclosure. According to an embodiment of the disclosure, the compensation device 300 may comprise a matching circuit configuration, and the compensation device 300 may be coupled to the stretchable lines of the physiological signal processing device. The matching circuit configuration may compensate the signal attenuation that is generated because the impedance is changed when the stretchable lines are stretched. Taking physiological signal processing device 100 for example, when the stretchable line 130A or the stretchable line 130B is stretched, the impedance ($Z_S$) of the stretchable line 130A or the stretchable line 130B will increase. Therefore, when the impedance ($Z_S$) of the stretchable line 130A or the stretchable line 130B increases, the signal received on the load may be attenuated and distorted due to the increase of the impedance ($Z_S$) of the stretchable line 130A or the stretchable line 130B. Taking mathematical formula for illustration, when the compensation device 300 is not configured in the physiological signal processing device, the voltage of the signal received by the load may be indicated as $$f(S) = V_0 + \left(\frac{Z}{Z_S + Z} \times V_S\right),$$

wherein $V_0$ is the initial voltage, $V_S$ is the voltage provided by the physiological signal processing device, $Z$ is the equivalent impedance of the circuit, and the $Z_S$ is the impedance of the stretchable line. Referring to the above formula, when the impedance $Z_S$ of the stretchable line is increased, the voltage of the signal received by the load will be decreased, i.e. the signal received on the load may be attenuated and distorted. Referring to FIG. 3, in the embodiment, when the compensation device 300 is configured in the physiological signal processing device, the voltage of the signal received by the load may be changed to $$f(S) = V_0 + \left[\left(\frac{Z + Z_C}{Z_S + Z + Z_C}\right) \times V_S\right] \times \left(\frac{Z_L}{Z_L + Z_O}\right),$$

wherein $V_O$ is the initial voltage, $V_S$ is the voltage provided by the physiological signal processing device, Z is the equivalent impedance of the circuit, the $Z_S$ is the impedance of the stretchable line, $Z_C$ is the equivalent impedance in the compensation device 300, $Z_L$ is the equivalent impedance of the load and the $Z_O$ is the equivalent output impedance of the compensation device 300. Referring to the above formula, the attenuation and distortion of the signal received by the load may be decreased by adjusting the equivalent impedance $Z_C$ in the compensation device 300. According to an embodiment of the disclosure, the compensation device 300 may be applied to the physiological signal processing device 100.

Figure 4:
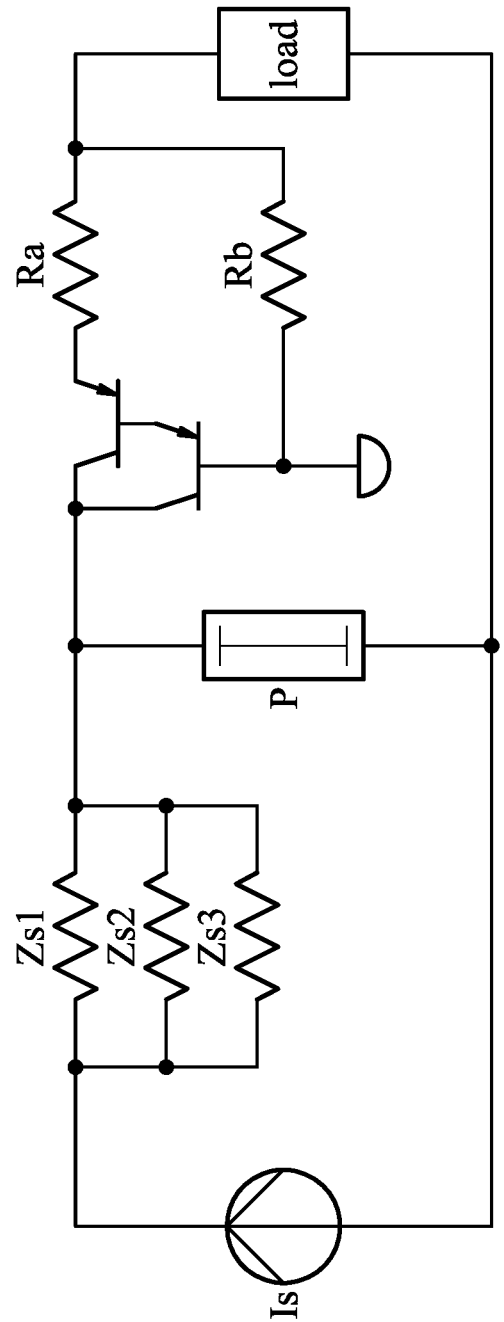
FIG. 4 is an equivalent schematic diagram of a compensation device 400 according to another embodiment of the disclosure.

FIG. 4 is an equivalent schematic diagram of a compensation device 400 according to another embodiment of the disclosure. According to an embodiment of the disclosure, the compensation device 400 may comprise a regulator circuit, and the compensation device 400 may be coupled to the stretchable lines of the physiological signal processing device. The regulator circuit may comprise a power transistor P, a first resistor $R_a$, and a second resistor $R_b$. The regulator circuit may compensate the noise interference that is generated because the impedance is changed when the stretchable lines are stretched. Taking physiological signal processing device 200 for example, when the stretchable lines 230A~230C are stretched, the impedances ($Z_S1$, $Z_S2$, $Z_S3$) of the stretchable lines 230A~230C will be changed, therefore, the noise signal generated by the stretchable lines 230A~230C will be changed accordingly. When the noise signal is changed, the voltage of the signal received by the load will be changed accordingly. That is to say, the voltage of the signal received by the load may be not stable due to the interference of the noise signal. Referring to FIG. 4, in the embodiment, when the compensation device 400 is configured in the physiological signal processing device, the voltage of the signal received by the load may be indicated as $$f(S) = V_0 + \left[\left(\frac{R_b}{R_a + R_b}\right) \times V_S\right] + 1.25.$$

Referring to the above formula, when the compensation device 400 is configured in the physiological signal processing device, the voltage of the signal received by the load could maintain in a fixed value by adjusting the first resistor $R_a$ and the second resistor $R_b$ of the compensation device 400. Therefore, it could be avoided that the voltage of the signal received by the load is changed due to the change of impedance of the stretchable lines, by adjusting the compensation device 400.

Figure 5:
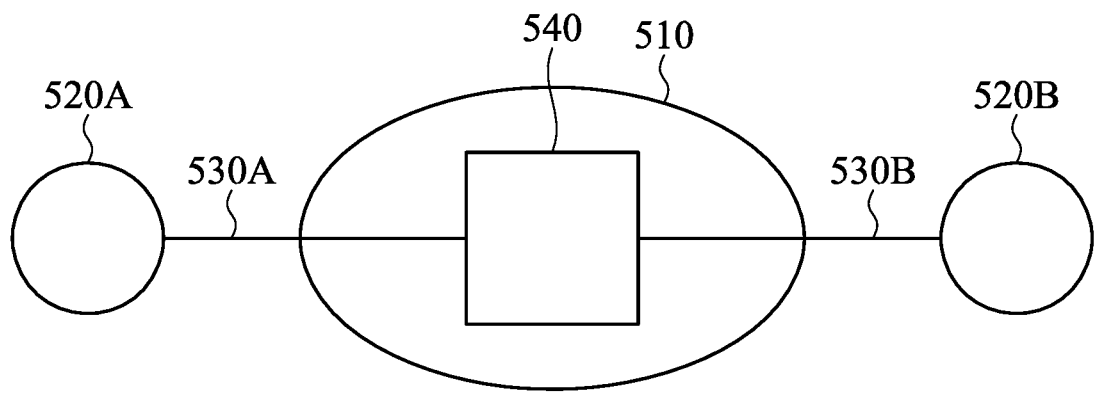
FIG. 5 is a schematic diagram of a physiological signal processing device 500 according to another embodiment of the disclosure.

FIG. 5 is a schematic diagram of a physiological signal processing device 500 according to another embodiment of the disclosure. As shown in FIG. 5, the physiological signal processing device 500 may comprise a patch 510, a first electrode 520A, a second electrode 520B, a first line 530A, a second line 530B, and a processing device 540. In order to clarify the concept of the disclosure, FIG. 5 presents a simplified block diagram in which the elements relevant to the disclosure are shown. However, the disclosure should not be limited to what is shown in FIG. 5.

According to an embodiment of the disclosure, the processing device 540 may be a microprocessor or a microcontroller, but the disclosure should not be limited thereto.

As shown in FIG. 5, unlike the physiological signal processing device 100, in the embodiment, the first line 530A and the second line 530B are not the stretchable lines. The first line 530A and the second line 530B is rolled into the patch 510, and the first line 530A and the second line 530B may be extended by a mechanical structure (not shown in figures) or an electric motor (not shown in figures) of the physiological signal processing device 500. In addition, as shown in FIG. 5, in the embodiment, the processing device 540 may be configured in the patch 510. The first electrode 520A and the second electrode 520B are respectively coupled to the processing device 540 through the first line 530A and the second line 530B. Because the operations of the processing device 540 are similar to the operations of the processing device 140 of the physiological signal processing device 100, the details will not be discussed again.

Figure 6:
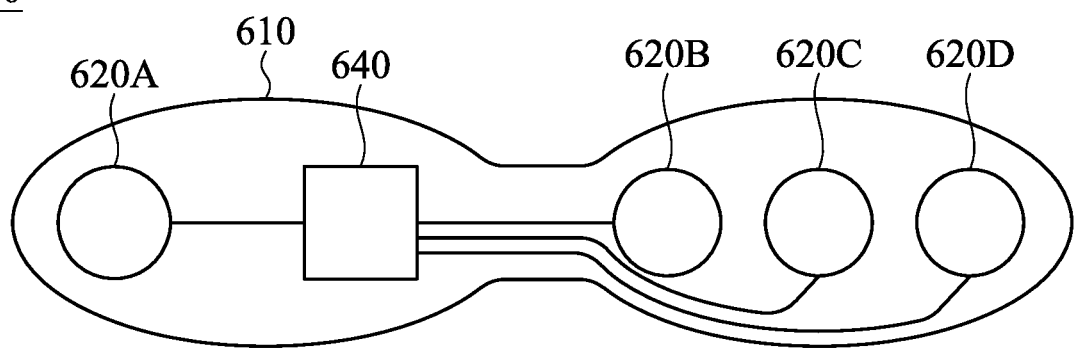
FIG. 6 is a schematic diagram of a physiological signal processing device 600 according to another embodiment of the disclosure.

FIG. 6 is a schematic diagram of a physiological signal processing device 600 according to another embodiment of the disclosure. As shown in FIG. 6, the physiological signal processing device 600 may comprise a patch 610, a first electrode 620A, a second electrode 620B, a third electrode 620C, a fourth electrode 620D, and a processing device 640. In order to clarify the concept of the disclosure, FIG. 6 presents a simplified block diagram in which the elements relevant to the disclosure are shown. However, the disclosure should not be limited to what is shown in FIG. 6. In some embodiments of the disclosure, the physiological signal processing device 600 may comprise different number of electrodes.

According to an embodiment of the disclosure, the processing device 640 may be a microprocessor or a microcontroller, but the disclosure should not be limited thereto.

According to an embodiment of the disclosure, the patch 610 may be made of the stretchable material. Furthermore, as shown in FIG. 6, according to an embodiment of the disclosure, the first electrode 620A is configured in the first side (e.g. left side) of the patch 610, and the second electrode 620B, the third electrode 620C and the fourth electrode 620D are configured in the second side (e.g. right side) of the patch 610. When the ECG signal measurement is performed for the user, the patch 610 of the physiological signal processing device 600 may be patched on the body of the user. According to an embodiment of the disclosure, when the patch 610 is patched on the body of the user, the processing device 640 may obtain the ECG signal from the first electrode 620A. Furthermore, the processing device 640 may select another electrode from the second electrode 620B, the third electrode 620C and the fourth electrode 620D, which are configured in the same side of the patch 610, to obtain the ECG signal. In other words, if the processing device 640 selects the second electrode 620B, the processing may obtain the ECG signals from the first electrode 620A and the second electrode 620B. According to an embodiment of the disclosure, when the position of the electrode needs to be adjusted, the processing device 640 may select another electrode from the third electrode 620C and the fourth electrode 620D, which are configured in the same side of the patch 610, to obtain the ECG signal. Because other operations of the processing device 640 are similar to the operations of the processing device 140 of the physiological signal processing device 100, the details will not be discussed again.

Figure 7A:
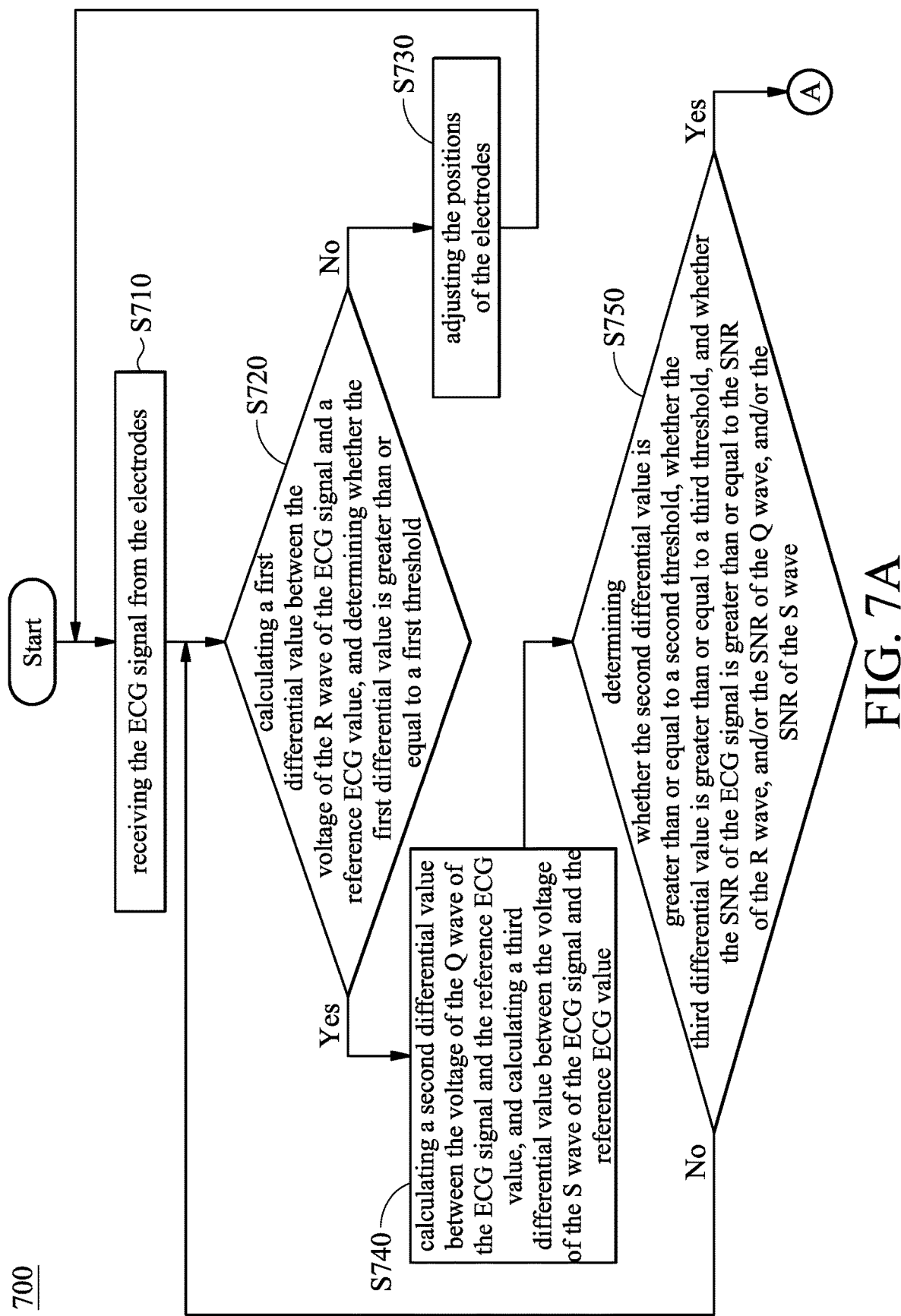
FIGS. 7A-7B is a flow chart 700 illustrating a physiological signal processing method according to an embodiment of the disclosure.
Figure 7B:
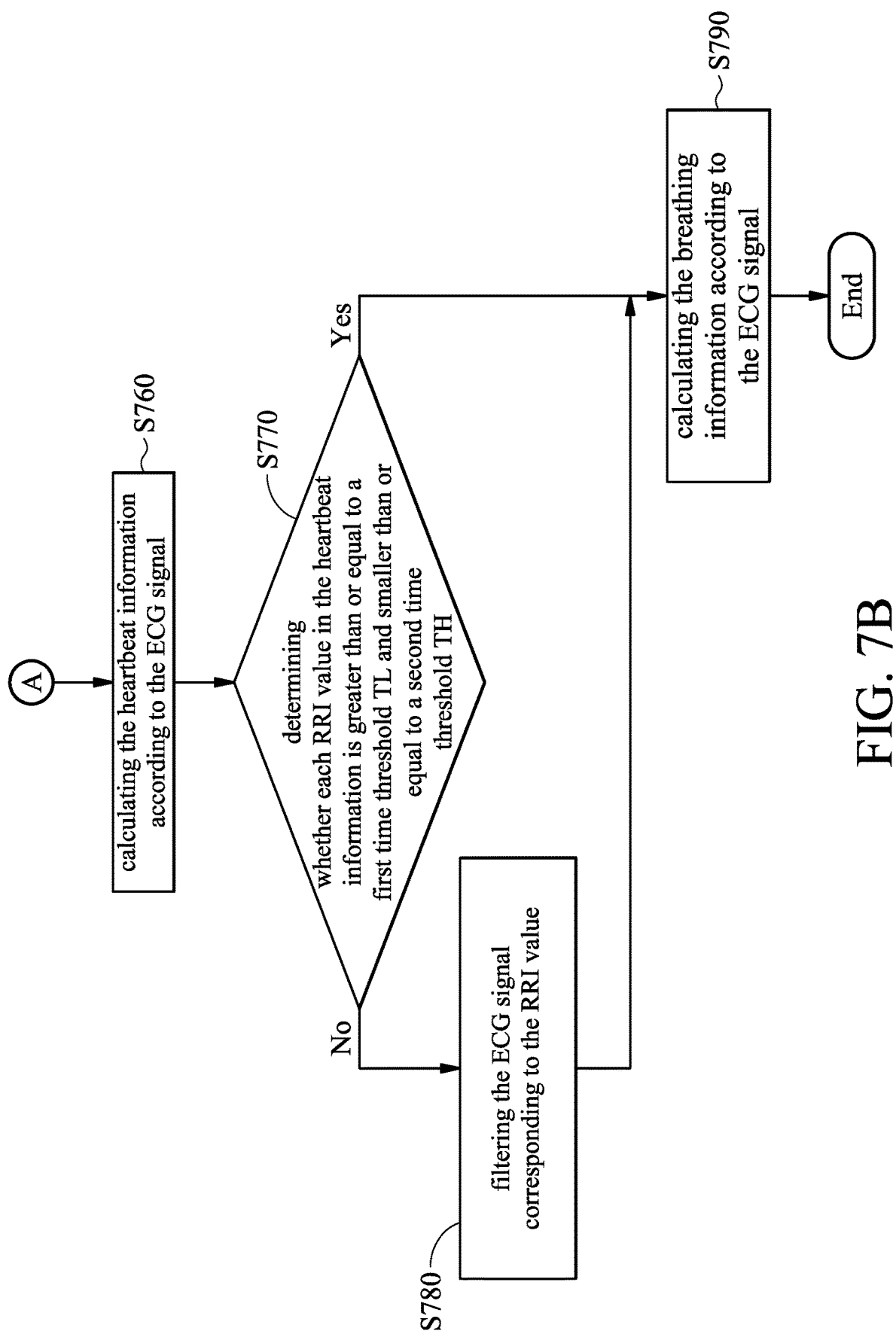

FIGS. 7A-7B is a flow chart 700 illustrating a physiological signal processing method according to an embodiment of the disclosure. The physiological signal processing method could be applied to the physiological signal processing devices 100, 200, 500 and 600. In step S710, when a plurality of electrodes of the physiological signal processing device are put (patched) on the body of user, the processing device of the physiological signal processing device may receive the ECG signal from the electrodes. In step S720, the processing device of the physiological signal processing device may calculate a first differential value between the voltage of the R wave of the ECG signal and a reference ECG value, and determine whether the first differential value is greater than or equal to a first threshold to determine whether to adjust the positions of the electrodes. When the first differential value is not greater than or equal to the first threshold, step S730 is performed. In step S730, the positions of the electrodes are adjusted (coarse adjustment). When the positions of the electrodes have been adjusted, the physiological signal processing method may return to step S710. When the first differential value is greater than or equal to the first threshold, step S740 is performed. In step S740, the processing device of the physiological signal processing device may calculate a second differential value between the voltage of the Q wave of the ECG signal and the reference ECG value, and calculate a third differential value between the voltage of the S wave of the ECG signal and the reference ECG value.

In step S750, the processing device of the physiological signal processing device may determine whether the second differential value is greater than or equal to a second threshold, whether the third differential value is greater than or equal to a third threshold, and whether the signal-to-noise ratio (SNR) of the ECG signal is greater than or equal to the SNR of the R wave, and/or the SNR of the Q wave, and/or the SNR of the S wave. When the second differential value is greater than or equal to the second threshold, the third differential value is greater than or equal to the third threshold, and the SNR of the ECG signal is greater than or equal to the SNR of the R wave, and/or the SNR of the Q wave, and/or the SNR of the S wave, step S760 is performed. In step S760, the processing device of the physiological signal processing device may calculate the heartbeat information according to the ECG signal. When the second differential value is not greater than or equal to the second threshold, the third differential value is not greater than or equal to the third threshold, or the SNR of the ECG signal is not greater than or equal to the SNR of the R wave, and/or the SNR of the Q wave, and/or the SNR of the S wave, the positions of the electrodes are adjusted (fine adjustment) and the physiological signal processing method may return to step S720.

In step S770, when the heartbeat information is obtained, the processing device of the physiological signal processing device may determine whether each RRI value in the heartbeat information is greater than or equal to a first time threshold TL and smaller than or equal to a second time threshold TH. When the RRI value is not greater than or equal to a first time threshold TL, or not smaller than or equal to a second time threshold TH, step S780 is performed. In step S780, the processing device of the physiological signal processing device may filter the ECG signal corresponding to the RRI value. When the RRI value is greater than or equal to a first time threshold TL and smaller than or equal to a second time threshold TH, step S790 is performed. In step S790, the processing device of the physiological signal processing device may calculate the breathing information according to the ECG signal.

According to an embodiment of the disclosure, in step S760, before using the heartbeat algorithms to generate the heartbeat information of the user, the processing device of the physiological signal processing device may determine whether to execute a smoothing algorithm for the ECG signal.

According to an embodiment of the disclosure, in step S790, after using the breathing algorithm to generate the breathing information of the user, the processing device of the physiological signal processing device may determine whether to enable a smoothing function for the breathing signal.

According to the physiological signal processing devices and methods provided in the embodiments of the disclosure, the distance (positions) of the electrodes could be adjusted for different body structures of different users. Therefore, according to the physiological signal processing devices and methods, when the single-lead measurement method is adopted to measure the ECG signal, the accuracy could be increased.

Use of ordinal terms such as "first", "second", "third", etc., in the disclosure and claims is for description. It does not by itself connote any order or relationship.

The steps of the method described in connection with the aspects disclosed herein may be embodied directly in hardware, in a software module executed by a processor, or in a combination of the two. A software module (e.g., including executable instructions and related data) and other data may reside in a data memory such as RAM memory, flash memory, ROM memory, EPROM memory, EEPROM memory, registers, a hard disk, a removable disk, a CD-ROM, or any other form of computer-readable storage medium known in the art. A sample storage medium may be coupled to a machine such as, for example, a computer/processor (which may be referred to herein, for convenience, as a "processor") such that the processor could read information (e.g., code) from and write information to the storage medium. A sample storage medium may be integral to the processor. The processor and the storage medium may reside in an ASIC. The ASIC may reside in user equipment. Alternatively, the processor and the storage medium may reside as discrete components in user equipment. Moreover, in some aspects any suitable computer-program product may comprise a computer-readable medium comprising codes relating to one or more of the aspects of the disclosure. In some aspects a computer program product may comprise packaging materials.

The above paragraphs describe many aspects of the disclosure. Obviously, the teaching of the disclosure could be accomplished by many methods, and any specific configurations or functions in the disclosed embodiments present a representative condition. Those who are skilled in this technology will understand that all of the disclosed aspects in the disclosure could be applied independently or be incorporated.

While the disclosure has been described by way of example and in terms of preferred embodiment, it is to be understood that the disclosure is not limited thereto. Those who are skilled in this technology could still make various alterations and modifications without departing from the scope and spirit of this disclosure. Therefore, the scope of the present disclosure shall be defined and protected by the following claims and their equivalents.

What is claimed is:

1. A physiological signal processing device, comprising:
a patch;
a plurality of electrodes, detecting an Electrocardiography (ECG) signal; and
a processing device, configured in the patch, coupled to the plurality of electrodes to receive the ECG signal, and according to the ECG signal, calculating a first differential value between a voltage of an R wave of the ECG signal and a reference ECG value, and determining whether the first differential value is greater than or equal to a first threshold to determine whether to adjust positions of the plurality of electrodes,
wherein when the positions of the plurality of electrodes are determined, the processing device obtain heartbeat information and/or breathing information according to the ECG signal.

2. The physiological signal processing device of claim 1, further comprising:
a plurality of stretchable lines, wherein a first electrode of the plurality of electrodes is coupled to the processing device through a first stretchable line of the plurality of stretchable lines, and a second electrode of the plurality of electrodes is coupled to the processing device through a second stretchable line of the plurality of stretchable lines.

3. The physiological signal processing device of claim 2, further comprising:
a first compensation device, coupled to the plurality of stretchable lines, and comprising a matching circuit configuration, wherein the first compensation device utilizes the matching circuit configuration to compensate signal attenuation that is generated because impedance is changed when the stretchable lines are stretched.

4. The physiological signal processing device of claim 1, further comprising:
a plurality of stretchable lines, configured in the patch, wherein the plurality of electrodes are configured in the patch and the plurality of electrodes are coupled to the plurality of stretchable lines.

5. The physiological signal processing device of claim 4, further comprising:
a second compensation device, coupled to the plurality of stretchable lines, and comprising a regulator circuit, wherein the second compensation device utilizes the regulator circuit to compensate noise interference that is generated because impedance is changed when the stretchable lines are stretched.

6. The physiological signal processing device of claim 1, further comprising:
a plurality of lines, rolled into the patch, wherein a first electrode of the plurality of electrodes is coupled to the processing device through a first line of the plurality of lines, and a second electrode of the plurality of electrodes is coupled to the processing device through a second line of the plurality of lines; and
a mechanical structure or an electric motor, coupled to the plurality of lines to control extensions of the plurality of lines.

7. The physiological signal processing device of claim 1, wherein the patch is made of a stretchable material, and one of the plurality of electrodes is configured in a first side of the patch, and other electrodes are configured in a second side of the patch.

8. The physiological signal processing device of claim 7, wherein the processing device selects one electrode from the electrodes configured in the second side of the patch to obtain the ECG signal.

9. The physiological signal processing device of claim 8, wherein when the positions of the plurality of electrodes need to be adjusted, the processing device selects another electrode from the electrodes configured in the second side of the patch to obtain the ECG signal.

10. The physiological signal processing device of claim 1, wherein when the first differential value is not greater than or equal to the first threshold, the positions of the plurality of electrodes are adjusted.

11. The physiological signal processing device of claim 1, wherein when the first differential value is greater than or equal to the first threshold, the processing device calculates a second differential value between a voltage of a Q wave of the ECG signal and the reference ECG value, and calculate a third differential value between a voltage of a S wave of the ECG signal and the reference ECG value.

12. The physiological signal processing device of claim 11, wherein the processing device determines whether the second differential value is greater than or equal to a second threshold, whether the third differential value is greater than or equal to a third threshold, and whether a signal-to-noise ratio (SNR) of the ECG signal is greater than or equal to the SNR of the R wave, and/or the SNR of the Q wave, and/or the SNR of the S wave.

13. The physiological signal processing device of claim 12, wherein when the second differential value is greater than or equal to the second threshold, the third differential value is greater than or equal to the third threshold, and the signal-to-noise ratio (SNR) of the ECG signal is greater than or equal to the SNR of the R wave, and/or the SNR of the Q wave, and/or the SNR of the S wave, the processing device calculates the heartbeat information and the breathing information according to the ECG signal.

14. The physiological signal processing device of claim 12, wherein when the second differential value is not greater than or equal to the second threshold, the third differential value is not greater than or equal to the third threshold, or the signal-to-noise ratio (SNR) of the ECG signal is not greater than or equal to the SNR of the R wave, and/or the SNR of the Q wave, and/or the SNR of the S wave, the positions of the plurality of electrodes are adjusted.

15. The physiological signal processing device of claim 1, wherein the processing device uses a plurality of heartbeat algorithms to calculate the heartbeat information according to the ECG signal.

16. The physiological signal processing device of claim 15, wherein the heartbeat information comprises RRI (R–R interval) values, heart rate (HR) and heart rate variability (HRV).

17. The physiological signal processing device of claim 16, wherein the processing device determines whether each RRI value is greater than or equal to a first time threshold and smaller than or equal to a second time threshold.

18. The physiological signal processing device of claim 17, wherein when the RRI value is not greater than or equal to a first time threshold or not smaller than or equal to a second time threshold, the processing device filters the ECG signal corresponding to the RRI value.

19. The physiological signal processing device of claim 16, wherein the processing device determines whether each RRI value is greater than or equal to a time threshold.

20. The physiological signal processing device of claim 16, wherein the processing device determines whether each RRI value is smaller than or equal to a time threshold.

21. The physiological signal processing device of claim 15, wherein before using the heartbeat algorithms to generate the heartbeat information, the processing device executes a smoothing algorithm for the ECG signal.

22. The physiological signal processing device of claim 1, wherein the processing device uses a breathing algorithm to calculate the breathing information according to the ECG signal.

23. The physiological signal processing device of claim 1, wherein the positions of the plurality of electrodes are determined according to a machine learning algorithm.

* * * * *